United States Patent [19]

Hofmann

[11] Patent Number: 4,824,662

[45] Date of Patent: Apr. 25, 1989

[54] NAIL POLISH REMOVER

[75] Inventor: William H. Hofmann, St. Louis, Mo.

[73] Assignee: Vi-Jon Laboratories, Inc., St. Louis, Mo.

[21] Appl. No.: 62,200

[22] Filed: Jun. 15, 1987

[51] Int. Cl.$^4$ .......................... A61K 7/47; C11D 1/94
[52] U.S. Cl. ...................................... 424/61; 252/546; 134/38
[58] Field of Search .................. 424/61; 252/546, 364; 134/38

[56] References Cited

U.S. PATENT DOCUMENTS 2,765,257 10/1956 Blackburn .............................. 424/61
4,485,037 11/1984 Curtis ................................. 424/61 X

FOREIGN PATENT DOCUMENTS 205527 11/1983 Japan .

Primary Examiner—Nancy A. B. Swisher
Attorney, Agent, or Firm—Gravely, Lieder & Woodruff

[57] ABSTRACT

A nail polish remover having an acetone or ethyl acetate-ethanol base and a hydrolyzed soy protein and surfactant combination as an additive to inhibit the dehydrating charactertistics of the remover on the nails and skin of the user.

3 Claims, No Drawings

NAIL POLISH REMOVER

BACKGROUND OF THE INVENTION

The present invention relates to a novel composition. More particularly, the present invention relates to a novel composition useful for removing nail lacquer.

Many compositions are known which are useful in removing lacquer, from fingernails or toenails. These compositions depend primarily upon the solvent action of acetone or acetone-like solvent to soften or dissolve the nail lacquer. After the lacquer has been dissolved or softened, it is usually removed by a gentle abrasive or by a gentle rubbing action.

In addition to acetone, ethyl acetate is a well known solvent used in nail polish removers.

These solvents readily remove the nail lacquer. However, when used alone they have a dehydrating effect on the nails of the user, rendering the nails dry, hard and succeptible to cracking and breaking.

Usually the solvents used in commercial nail polish removers all contain other materials, such as water and/or various oils, which not only lower the dehydrating effect of the solvents, but also lower the enamel dissolving efficiency of the solvents.

The object of this invention is to provide an efficient enamel dissolving system that minimizes the dehydration of skin and nails to which it is applied. Another object of this invention is to provide a unique combination of additives to a nail polish remover that does not interfere with the enamel dissolving properties of the solvents used and enhances the water retention of skin and nails.

I am aware of U.S. Pat. No. 4,485,037 which lowers water removal activity of nail polish removers based on acetone by adding collagen in combination with an acid addition salt of amidized trialkylamine cationic surfactant.

U.S. Pat. No. 4,302,464 describes a creamy nail lacquer remover containing a chelating agent, a suitable humectant, propylene glycol, 2-hydroxy-4-methoxybenzophenone-5-sulfonic acid, a collagen-derived protein-fatty acid condensation product and a carboxy vinyl polymer. This material too has an acetone base.

The present invention involves the use of a water soluble amine sale of a fatty acid amide of a hydrolyzed soy protein incorporated into an acetone or ethyl acetate based solvent system in an amount to reduce substantially the removal of moisture from the skin and nails of the user by the solvent systems involved. The soy protein based additive is an improvement over a collagen based additive because soy protein contains all of the essential amino acids whereas collagen is incomplete and missing several essential amino acids. The soy protein results in healthier looking, i.e., shining, lustrous, and moist, keratin substrates, such as nails, skin and hair.

Accordingly, it is a principal object of this invention to provide a nail polish remover which includes a water soluble soy protein based additive which substantially reduces the skin and nail water removing properties of the solvent system.

A further object is to provide a combination acetone or ethyl acetate based surfactant and a hydrolyzed soy protein addition to a nail polish remover which minimizes the dehydrating effects of the solvents on the nails and skin of the user.

These and other objects and advantages will become apparent hereinafter.

SUMMARY OF THE INVENTION

This invention relates to nail polish remover formulations containing, in addition to their solvent and modifier systems, an amount of a water soluble amine salt of a fatty acid amide of a hydrolyzed soy protein which will reduce substantially the skin and nail moisture removal of the solvent systems incorporated in the formulations.

The invention also consists in the parts and in the arrangements and combinations of parts hereinafter described and claimed.

DETAILED DESCRIPTION

In all of the examples and discussion which follows, all percentage figures are percent-by-weight of the finished formulation.

The nail enamel removers of this invention are primarily of two types, as follows:

1. Ethyl acetate base which consists of:
   Ethyl Acetate 82–88%
   Ethanol 12–18%
   A mixture of oils 1–2%
   The evaporated total solids of all conditioners is about 2.5/3.5%

2. Acetone base which consists of:
   Acetone 85/90%
   Water 10/15%
   Conditioners 0.20/0.50%
   The evaporated total solids of all conditioners is about 0.15/0.25%

The object of this invention is a combination, in either of the foregoing nail enamel remover bases, of a mixture composed of a surfactant, cocoamidopropyl dimethylamine propionate used at the 0.10% to 0.30% level and aminomethylpropanol salt of isostearic hydrolyzed soy protein used at the 0.05% to 0.25% level depending on the type of solvent base employed. The object of the use of this combination of ingredients is to provide a solvent based nail enamel remover system with the proper level of additives which shows an affinity for cuticle material, thus minimizing the dehydrating effects of the solvents necessary to dissolve the cured enamel film.

The combination of a surfactant, in this illustration cocamidopropyl dimethylamine propionate, with a hydrolyzed soy protein, in this illustration, AMP isotearic hydrolyzed soy protein will produce a hydrolyzed salt which has a conditioning and protective effect on the skin and nails.

The polish removers of this invention are characterized by the presence in solution of an amidized soya protein hydrolyzate. This process makes the protein totally anionic rather than amphoteric.

Soya protein hydrolyzates are relatively new materials for use in cosmetic preparations. They are made from either a soy isolate, a relatively pure plant derived protein extracted from soya beans, or, from a soya flour which is made by crushing soya beans and extracting the protein present during the hydrolysis process. Soya beans contain roughly 40% protein and 60% carbohydrate (starch). Soya bean isolate, the preferred starting material as the starchy materials have been removed, is extracted from the soy flour by a complex washing process which separates the protein from the carbohydrate or starchy materials.

It is important in cosmetic ingredients which have to be light in color and low in odor, to remove all the starchy materials, otherwise these will react with the terminal amino groups present in the soy protein giving rise to the Maillard reaction. When this happens dark brown odiferous products are formed—generally speaking, highly undesirable in cosmetic products. Hence, it is preferred that a pure soy protein isolate is used.

Soya protein hydrolyzates made from soya protein isolates are excellent conditioning materials for the skin, hair and nails (any keratinized body surface layer) as they form moisture retentive films which will help the substrate hold more moisture than it would normally. Soya proteins contain all the essential amino acids and represent a completely balanced product from a nutritional viewpoint. Commonly used cosmetic proteins are normally collagen based and collagen is deficient in the essential amino acid tryptophane. For healthy skin, hair and nails it is necessary to use products with a complete complement of essential amino acids, as found in soya proteins.

Hydrolyzed soya proteins, when topically applied, have the following beneficial properties to the skin and hair:

(a) It forms smoothing films, helping to minimize roughness and wrinkles.
(b) It will have a protective colloid effect.
(c) It forms a moisture retentive film on the surface of the skin which will help plump 'normal' dry skin, improving its elasticity and suppleness.
(d) It combats chapping and irritation caused by detergents.
(e) It forms skin smoothing films, reducing the roughness of the nail.
(f) It forms a moisture retentive film on the nail, which will increase the moisture content of the nail, improving flexibility.
(g) It protects, through the protective colloid effect, the nail from environmental damage (pollutants, soap, cleansing compounds) which will remove the essential cementing lipids in the matrix from the nail keratin.
(h) It improves the surface shine of the nail.

It is important to emphasise that the foregoing properties are present only in a hydrolyzed soya protein with an average molecular weight of 1,000 to 4,000.

Hydrolyzed soy proteins hereinbefore described are only water woluble and compatible with up to 50% aqueous alcohol. They are not compatible with conventional nail polish removers without further treatment.

To achieve compatibility with aqueous acetone, a further processing step, amidization of the protein is required. This can be substantially represented by the following formula:

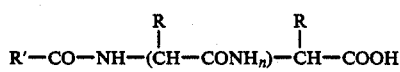

$R'$ = Fatty Acid of 5–22 carbons (preferably isostearic acid - 18 carbons)
$R$ = Side-chain groups characterisitc of amino acids in soya protein
$n$ = Integer from 10 to 40

The conversion of accessible primary amine groups of hydrolyzed soya protein (including the sidechain or epsilon amino groups, such as Arginine and Lysine—a key essential amino acid) to amide groups, imparts an anionic charge to the hydrolyzed soy protein. This enables it to form stable salts with bases: organic amines, such as alkyl and hydroxyalkyl amines of 1–4 carbon atoms, e.g., trimethylamine, diethylamine, etc; and alkanolamines of 1–4 carbon atoms, such as, ethanolamine, propanolamine, aminomethylpropanol, etc. The exact nature of the amine which forms the salt is not critical, as long as the sale formed is cosmetically acceptable and is soluble in aqueous acetone.

The preferred product is a salt of a fatty acid amide of hydrolyzed soy protein, i.e., the aminomethylpropanol salt of isostearic amide of hydrolyzed soya isolate protein. This product is available from Brooks Industries Inc. 70 Tyler Place, South Plainfield, N.J. 07080, under the trademark of "Etha-Soy Iso" as a light yellow clear liquid with a solids content of 27–35% (after drying for 16 hours at 105° C.), a pH 7.0–9.5 (10% aqueous solution at 25° C.), a specific gravity of 0.830–0.880 (at 25° C.), and an acid value of 35.0–50.0.

The presence of this derivative of hydrolyzed soy protein, in conjunction with the amidoamine salt, will substantially reduce the propensity of the acetone based polish remover to remove water from the nails of the user. Moreover, the combination imparts a water loss resisting film on the nails superior to that produced by either ingredient alone.

This invention is intended to cover all changes and modifications of the example of the invention herein chosen for purposes of the disclosure which do not constitute departures from the spirit and scope of the invention.

What is claimed is:

1. A nail polish remover composition having an active ingredient selected from the group consisting of ethyl acetate and acetone and containing as essential ingredients the combination about 0.1 to about 0.3% by weight of a surfactant and about 0.05 to about 0.25% by weight of a cosmetically acceptable amidoamine salt of hydrolyzed soy protein having a molecular weight of 1000–4000 and containing all of the essential amino acids for healthy looking keratin substrates, said soy protein being effective to substantially reduce the skin and nail water removal properties of the active ingredient in the nail polish remover.

2. The nail polish remover of claim 1 wherein the surfactant is cocoamidopropyl dimethylamine propionate.

3. The nail polish remover of claim 1 wherein the hydrolyzed soy protein is aminomethylpropanol isostearic hydrolyzed soy protein.

* * * * *